US00PP36720P2

(12) United States Plant Patent
Hansen

(10) Patent No.: US PP36,720 P2
(45) Date of Patent: Jun. 3, 2025

(54) ***TRADESCANTIA* PLANT NAMED 'Webmaster'**

(50) Latin Name: ***Tradescantia* x *andersoniana***
Varietal Denomination: Webmaster

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,039

(22) Filed: May 13, 2024

(51) Int. Cl.
*A01H 5/02* (2018.01)
*A01H 6/00* (2018.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP15,971 P2 * 9/2005 van Noort ..... Plt./263.1

OTHER PUBLICATIONS https://www.northshoreplantclub.com/plant?ID=23916; "Webmaster Spiderwort"; (retrieved from the Internet on Aug. 27, 2024).*

* cited by examiner

*Primary Examiner* — Susan McCormick Ewoldt

(57) ABSTRACT

A new and distinct plant cultivar of *Tradescantia* plant named 'Webmaster' characterized by glaucous, bluish-green, lanceolate foliage of season. The large flowers of rounded petals with warm purple in the center transitioning to near white along the edges appearing over a 22-week long period beginning late May and continuing through mid-autumn. The new plant is suitable for landscaping as a specimen or en masse.

1 Drawing Sheet

Botanical classification: *Tradescantia* x andersoniana.
Varietal denomination: 'Webmaster'.

STATEMENT REGARDING PRIOR DISCLOSURES UNDER 37 CFR 1.77(b)(6)

*Tradescantia* 'Webmaster' was first sold on Feb. 5, 2024. No plants of 'Webmaster' have been sold or offered for sale in this country or anywhere in the world nor has any disclosure of the new plant been made more than one year prior the filing date of this application.

BACKGROUND OF THE PLANT

The present invention relates to a new and distinct spiderwort plant, *Tradescantia* 'Webmaster' hereinafter also referred to as the "new plant" or just the cultivar name, 'Webmaster'. The new plant was a self-pollination of an unnamed selection in a isolation block at a wholesale perennial nursery in Zeeland, Michigan, in the spring of 2020. The seeds from the unnamed plant were harvested and planted later in 2020. The individual seedling that became named 'Webmaster' was previously assigned the breeder code 20-1-1 in the evaluation process.

The new plant has been asexually propagated by stem cuttings, node cuttings and division at the same nursery in Zeeland, Michigan, USA since 2021 with the resultant asexually propagated plants having retained all the same traits as the original plant. 'Webmaster' is stable and reproduces true to type in successive generations of asexual reproduction.

SUMMARY OF THE INVENTION

The new *Tradescantia* variety of the present invention is a member of the Commelinaceae family and passed initial evaluation in the summer of 2021 as a seedling growing in the trial garden of a wholesale perennial nursery in Zeeland, Michigan, U.S.A.

The nearest comparison varieties are 'Bilberry Ice' (not patented) and 'Pink Chablis' U.S. Plant Pat. No. 15,971.

'Pink Chablis' is about half the height, and the flowers are near white around the edges with more purplish pink toward the center. 'Bilberry Ice' has a shorter habit and the flowers have a broader white edge and narrower light purplish-pink center.

The parent plant was not maintained in either photography or plants, so no comparison is possible.

The following traits of *Tradescantia* 'Webmaster' in combination distinguish the new plant from all other spiderworts known to the inventor:

1. Rounded mound habit;
2. Lanceolate, glaucous foliage of bluish-green;
3. Large single flowers with rounded petals of warm purple in the center transitioning to white along the edges appearing over a prolonged season beginning in late May in Michigan and continuing until mid-autumn.

BRIEF DESCRIPTION OF THE DRAWINGS

The drawings of the new plant demonstrate the overall appearance and unique traits of 'Webmaster' as a one-year-old plant grown in a full-sun field near Zeeland, MI with supplemental water and fertilizer provided as needed. The colors are as accurate as reasonably possible with color reproductions. Variation in ambient light spectrum, source, and direction may cause the appearance of minor variations in color.

DETAILED BOTANICAL DESCRIPTION

Figure 1:
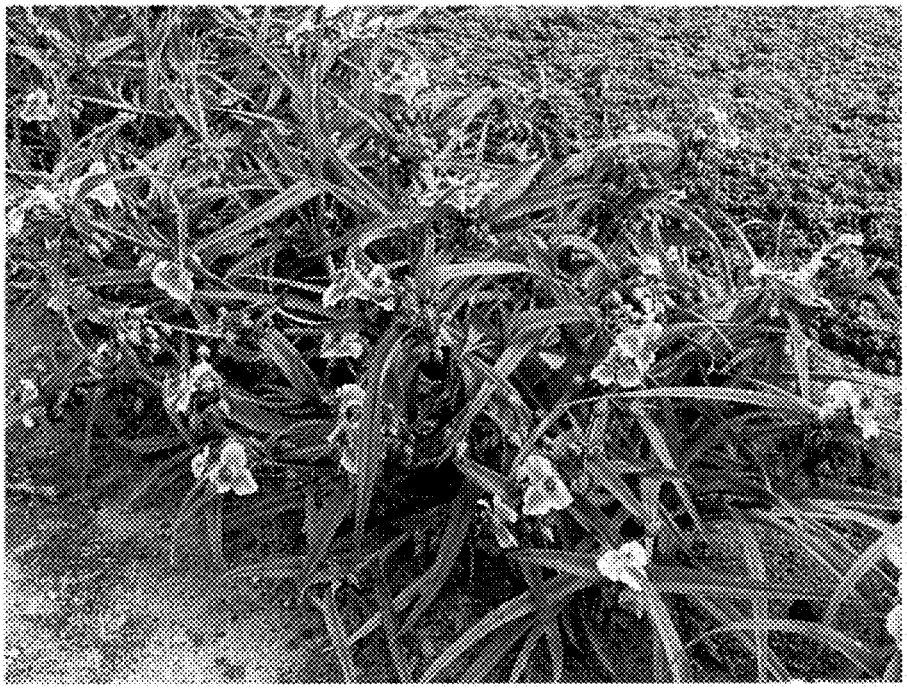
FIG. 1 shows the plant in the open in mid-summer.
Figure 2:
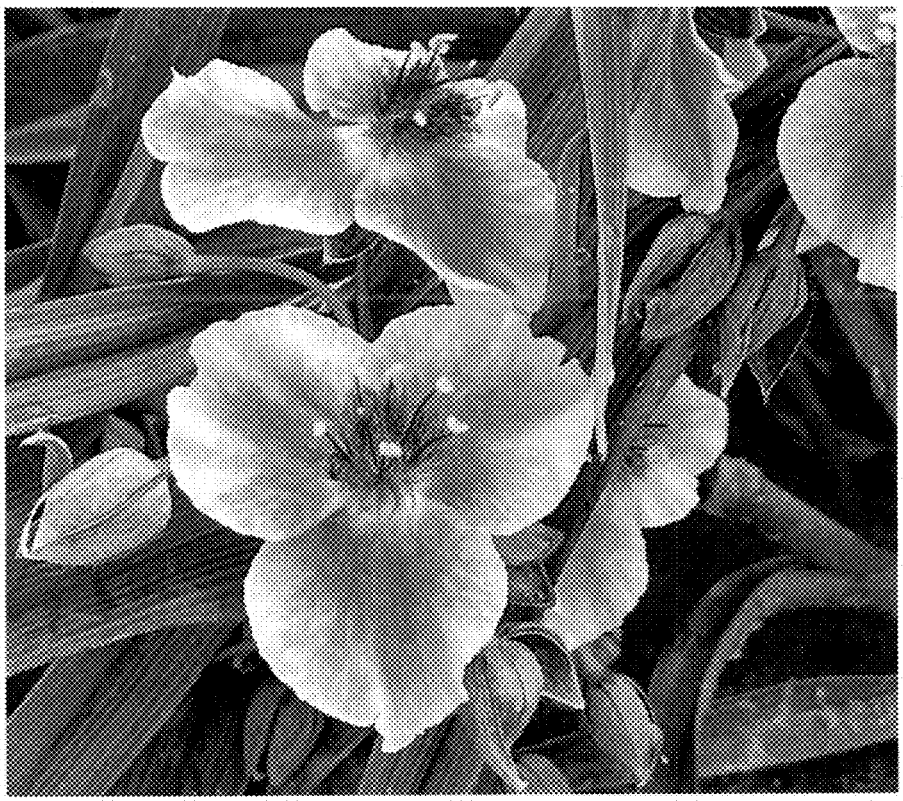
FIG. 2 shows a close-up of the buds and flowers from different angles.

The following detailed descriptions and color references of the new cultivar are based on the 2001 edition of The Royal Horticultural Colour Chart except where common dictionary terms are used. The plant described is a two-year-old plant grown in a full-sun display garden and a one-year-old plant grown in a partially shaded greenhouse in Zeeland, Michigan with supplemental water and fertilizer. *Tradescantia* 'Webmaster' has not been observed under all possible environments. The phenotype may vary slightly with different growing environments such as temperature, light, fertility, soil pH, moisture, and maturity levels, but without any change in the genotype.

Botanical classification: *Tradescantia* hybrid;

Parentage: The parent is an unnamed selection;

Plant habit: Low bushy mound, winter-hardy herbaceous perennial;

Size: To about 30 cm tall and about 103 cm across including foliage and flowers;

Leaves: Sessile; alternate; linear; conduplicate; arching; slightly glaucous abaxial and adaxial; adaxial puberulent along about 1.5 mm of margin; micro-serrulate margin; narrowly acute apex and decurrent base;

Leaf size: Up to about 51 cm long and about 20 mm across, average about 32 cm long and 17 mm across;

Leaf color: Young 0.5 mm margin of abaxial and adaxial leaves nearest RHS 187A; young adaxial between RHS 138A and RHS 137B; young abaxial nearest RHS N138C; mature adaxial between RHS 138A and RHS 138B and mature abaxial nearest RHS 191B;

Venation: Parallel; abaxial and abaxial midrib and primary veins glabrous;

Vein color: Young adaxial midrib nearest RHS 139A and secondary veins nearest RHS 137B, young abaxial midrib nearest RHS 146B and secondary veins nearest RHS 137A; mature adaxial midrib and secondary veins nearest RHS 137B, mature abaxial midrib and secondary veins nearest RHS 138A;

Petiole: Absent;

Inflorescence: In terminal and axillary clusters; with 12 to 58 flowers; average about 28;

Flowering season: Late May into mid-autumn for up to 22 weeks;

Peduncle: Absent;

Pedicels: Terete; outright; glabrous; strong and stiff; upon opening about 15 mm and 1 mm diameter, developing to about 33 mm long and about 1 mm diameter in the 7 to 10 days after petal drop;

Pedicel color: Base nearest RHS 157D and distally nearest RHS 59B;

Buds: Partially flattened ovoid; about 14 mm long and 7 mm wide;

Bud color: Exposed petals nearest RHS 85D, sepals nearest RHS 147B distally and nearest RHS 147C proximally, with margins and veins showing moderate blush of nearest N186C;

Flower: Single; perfect; incomplete; actinomorphic; to about 50 mm across and about 28 mm deep; no fragrance observed;

Flower lastingness: About one day;

Petals: Three; orbicular; rounded to broadly acute apex; rounded base; entire margin; glabrous both adaxial and abaxial; margin irregularly sinuate to slightly folded longitudinally, not typically flat;

Petal size: To about 26 mm long and 26 mm across near middle;

Petal color: Adaxial between RHS N81B and RHS N82B in the longitudinal center, the edge nearest RHS NN155D with the transition maculate in decreasing intensity, and the basal 3 mm nearest RHS NN155D; abaxial longitudinal center in proximal half between RHS 85D and RHS NN155D with distal half and outer 6 mm of margin between RHS N82C and RHS N82D; no change in color from first opening to closing;

Sepal: Typically three; ovate; concavo-convex; acute apex; truncate base; margins entire; adaxial surfaces glabrous; abaxial surface puberulent to pubescent; about 14 mm long and about 7 mm across;

Sepal color: Adaxial nearest RHS N186D with some patches of nearest RHS 146B; abaxial nearest RHS 147B with a moderate blush and veins of nearest RHS 59B;

Androecium: Stamen six;

*Filament*.—Six, terete; about 10 mm long and about 0.5 mm diameter; color proximal 1.5 mm nearest RHS NN155D, distally between RHS 86A and RHS N88A.

*Filament hairs*.—About 50 fine hairs originating in the proximal half of the filament; to about 7 mm long and less than 0.1 mm diameter; color nearest RHS 86B.

*Anther*.—Reniform to ovoid; basifixed; longitudinal; about 3 mm long, about 1.5 mm across, and 1 mm thick; color nearest RHS 9B.

*Pollen*.—Abundant; color nearest RHS 14BA.

Gynoecium: Single;

*Style*.—Terete; about 10 mm long and 0.3 mm diameter; color nearest 85D in proximal 1 mm, nearest RHS N92D distally.

*Stigma*.—Round with flat apex; about 0.5 mm diameter; color nearest RHS 91B.

*Ovary*.—Superior; about 3 mm long and 1.5 mm diameter; color between RHS 145C and RHS 147D.

Fruit and seeds: None observed;

Stem: Terete; glabrous; glaucous; mostly upright; strong and flexible; frequently bent at nodes in about a 10 to 25-degree angle; about 52 cm long and 10 mm diameter at base;

Stem color: Nearest RHS 138B;

Node: Typically swollen above to about 13 mm diameter; average internode 10 cm long; about 6 nodes per stem; average internode distance about 9.6 cm;

Node color: Nearest RHS 138B, typically same as surrounding stem;

Resistance to diseases and pests: Resistance to pests and diseases beyond that which is typical for spiderwort has not been observed.

*Tradescantia* 'Webmaster' is winter hardy to at least USDA zone 3.

It is claimed:

1. A new and distinct cultivar of a *Tradescantia* hybrid plant named 'Webmaster' substantially as herein described and illustrated.

* * * * *